(12) United States Patent
Hsieh et al.

(10) Patent No.: US 6,529,576 B2
(45) Date of Patent: Mar. 4, 2003

(54) METHOD AND APPARATUS FOR PITCH-ADAPTIVE RECONSTRUCTION IN MULTISLICE HELICAL COMPUTED TOMOGRAPHIC SYSTEMS

(75) Inventors: Jiang Hsieh, Brookfield, WI (US); Kishore C. Acharya, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/897,173

(22) Filed: Jun. 29, 2001

(65) Prior Publication Data
US 2003/0007604 A1 Jan. 9, 2003

(51) Int. Cl.$^7$ ................................. A61B 6/03
(52) U.S. Cl. ................. 378/15; 378/4; 378/19
(58) Field of Search ................. 378/4, 8, 15, 19, 378/901

(56) References Cited

U.S. PATENT DOCUMENTS

| | | | |
|---|---|---|---|
| 6,233,308 B1 | | 5/2001 | Hsieh |
| 6,351,514 B1 | * | 2/2002 | Besson ................. 378/15 |
| 6,452,996 B1 | * | 9/2002 | Hsieh ................... 378/15 |
| 2002/0122528 A1 | * | 9/2002 | Besson ................... 378/4 |

* cited by examiner

Primary Examiner—David V. Bruce
(74) Attorney, Agent, or Firm—Carl B. Horton, Esq.; Armstrong Teasdale LLP (57) ABSTRACT

One aspect of the present invention is a method that includes helically scanning an object at a selected helical pitch to acquire projection data of the object. The acquired projection data includes conjugate samples from single rows of the detector array of the CT imaging system and interrow samples. Projections in a plane of reconstruction (POR) are estimated based upon a selection of the projection data from the group consisting of the conjugate samples from at least one of the single rows, the interrow samples, and combinations thereof, the selection dependent upon the selected helical pitch. The estimated projections are filtered and backprojected to reconstruct at least one image of the object.

28 Claims, 6 Drawing Sheets

METHOD AND APPARATUS FOR PITCH-ADAPTIVE RECONSTRUCTION IN MULTISLICE HELICAL COMPUTED TOMOGRAPHIC SYSTEMS

BACKGROUND OF THE INVENTION

This invention relates generally to methods and apparatus for image reconstruction, and more particularly to methods and apparatus for adaptive image reconstruction for helical scans in multislice computed tomographic imaging systems.

Because of the non-robustness of multisector reconstruction methods, single sector reconstruction methods are often selected for cardiac computed tomographic (CT) imaging. In this reconstruction mode, a channel-dependent linear interpolation is used to estimate a set of projections at a plane of reconstruction (POR). The resulting projections are then weighted by a halfscan algorithm prior to filtering and backprojecting.

Investigations have revealed that slice sensitivity profiles (SSPs) for such reconstructions are significantly degraded at lower helical pitches. In particular, degraded contrast for small structures and an increased effect of partial volume have been noted.

BRIEF SUMMARY OF THE INVENTION

There is therefore provided, in one embodiment of the present invention, a method for reconstructing an image of an object utilizing a computed tomographic imaging system having a rotating gantry, a multirow detector array on the rotating gantry, and a radiation source on the rotating gantry configured to project a beam of radiation towards the detector array through an object to be imaged. The method includes helically scanning an object at a selected helical pitch to acquire projection data of the object, the projection data including conjugate samples from single rows of the detector array and interrow samples; estimating projections in a plane of reconstruction (POR) based upon a selection of the projection data from the group consisting of the conjugate samples from at least one of the single rows, the interrow samples, and combinations thereof, the selection dependent upon the selected helical pitch; and filtering and backprojecting the estimated projections to reconstruct at least one image of the object.

There is also provided, in another embodiment of the present invention, a method for reconstructing an image of an object utilizing a computed tomographic imaging system having a rotating gantry, a multirow detector array on the rotating gantry, and a radiation source on the rotating gantry configured to project a beam of radiation towards the detector array through an object to be imaged. The method includes helically scanning an object at a selected helical pitch to acquire projection data of the object, the projection data including conjugate samples from single rows of the detector array and interrow samples; estimating projections in a plane of reconstruction based upon a selection of the projection data from the group consisting of the conjugate samples from at least one of the single rows, the interrow samples, and combinations thereof, the selection dependent upon the selected helical pitch; weighting samples of the projection data according to a distance between a corresponding conjugate sampling pair and corresponding interrow sampling pair when a combination of the conjugate samples from at least one of the single rows and the interrow samples is selected; and filtering and backprojecting the weighted samples to reconstruct at least one image of the object.

In yet another embodiment of the present invention, there is provided a method for reconstructing an image of an object utilizing a computed tomographic imaging system having a rotating gantry, a multirow detector array oil the rotating gantry, and a radiation source on the rotating gantry configured to project a beam of radiation towards the detector array through an object to be imaged. This embodiment includes helically scanning an object at a selected helical pitch to acquire projection data of the object, the projection data including conjugate samples from single rows of the detector array and interrow samples; reconstructing an image of the object utilizing the conjugate samples; reconstructing an image of the object utilizing the interrow samples; and combining the image reconstructed utilizing the conjugates samples and the image reconstructed utilizing the interrow samples according to a pitch-dependent weighting function.

In still another embodiment, the present invention provides a computed tomographic imaging system having a rotating gantry, a multirow detector array on the rotating gantry, and a radiation source on the rotating gantry configured to project a beam of radiation towards the detector array through an object to be imaged. The system is configured to helically scan an object at a selected helical pitch to acquire projection data of the object, the projection data including conjugate samples from single rows of said detector array and interrow samples; and estimate projections in a plane of reconstruction based upon a selection of the projection data from the group consisting of the conjugate samples from at least one of the single rows, the interrow samples, and their combination, the selection dependent upon the selected helical pitch; and filter and backproject the estimated projections to reconstruct at least one image of the object.

Yet another embodiment of the present invention provides a computed tomographic imaging system having a rotating gantry, a multirow detector array on the rotating gantry, and a radiation source on the rotating gantry configured to project a beam of radiation towards the detector array through an object to be imaged. The system is configured to helically scan an object at a selected helical pitch to acquire projection data of the object, the projection data including conjugate samples from single rows of the detector array and interrow samples; estimate projections in a plane of reconstruction based upon a selection of the projection data from the group consisting of the conjugate samples from at least one of the single rows, the interrow samples, and combinations thereof, the selection dependent upon the selected helical pitch; weight samples of the projection data according to a distance between a corresponding conjugate sampling pair and corresponding interrow sampling pair when a combination of the conjugate samples from at least one of the single rows and the inter-row samples is selected; and filter and backproject the weighted samples to reconstruct at least one image of the object.

In yet another embodiment of the present invention, there is provided a computed tomographic imaging system having a rotating gantry, a multirow detector array on the rotating gantry, and a radiation source on the rotating gantry configured to project a beam of radiation towards the detector array through an object to be imaged. The system is configured to helically scan an object at a selected helical pitch to acquire projection data of the object, the projection data including conjugate samples from single rows of the detector array and interrow samples; reconstruct an image of the object utilizing the conjugate samples; reconstruct an image of the object utilizing the interrow samples; and combine the image reconstructed utilizing the conjugates samples and the image reconstructed utilizing the interrow samples according to a pitch-dependent weighting function.

Still another embodiment of the present invention provides a device for reconstructing an image of an object utilizing projection data acquired from a helical scan of the object at a selected pitch utilizing a computed tomographic imaging system having a multislice detector array with a plurality of rows, the projection data including both conjugate samples from single rows of the detector array and interrow samples. The device is configured to estimate projections in a plane of reconstruction based upon a selection of the projection data from the group consisting of the conjugate samples from at least one of the single rows, the interrow samples, and combinations thereof, the selection dependent upon the selected helical pitch; and filter and backproject the estimated projections to reconstruct at least one image of the object.

In another embodiment of the present invention, there is provided a device for reconstructing an image of an object utilizing projection data acquired from a helical scan of the object at a selected pitch utilizing a computed tomographic imaging system having a multislice detector array with a plurality of rows, the projection data including both conjugate samples from single rows of the detector array and interrow samples. The device is configured to estimate projections in a plane of reconstruction based upon a selection of the projection data from the group consisting of the conjugate samples from at least one of the single rows, the interrow samples, and combinations thereof, the selection dependent upon the selected helical pitch; weight samples of the projection data according to a distance between a corresponding conjugate sampling pair and corresponding interrow sampling pair when a combination of the conjugate samples from at least one of the single rows and the interrow samples is selected; and filter and backproject the weighted samples to reconstruct at least one image of the object.

Yet another embodiment of the present invention provides a device for reconstructing an image of an object utilizing projection data acquired from a helical scan of the object at a selected pitch utilizing a computed tomographic imaging system having a multislice detector array with a plurality of rows, the projection data including both conjugate samples from single rows of the detector array and interrow samples. This device is configured to estimate projections in a plane of reconstruction based upon a selection of the projection data from the group consisting of the conjugate samples from at least one of the single rows, the interrow samples, and combinations thereof, the selection dependent upon the selected helical pitch; reconstruct an image of the object utilizing the conjugate samples; reconstruct an image of the object utilizing the interrow samples; and combine the image reconstructed utilizing the conjugates samples and the image reconstructed utilizing the interrow samples according to a pitch-dependent weighting function.

There is also provided, in yet another embodiment of the present invention, a machine-readable medium having recorded thereon instructions configured to direct a computer to input projection data acquired from a helical scan of the object at a selected pitch utilizing a computed tomographic imaging system having a multislice detector array with a plurality of rows, the projection data including both conjugate samples from single rows of the detector array and interrow samples; estimate projections in a plane of reconstruction (POR) based upon a selection of the projection data from the group consisting of the conjugate samples from at least one of the single rows, the interrow samples, and combinations thereof, the selection dependent upon the selected helical pitch; and filter and backproject the estimated projections to reconstruct at least one image of the object.

Still another embodiment of the present invention provides a machine-readable medium having recorded thereon instructions configured to direct a computer to input projection data acquired from a helical scan of the object at a selected pitch utilizing a computed tomographic imaging system having a multislice detector array with a plurality of rows, the projection data including both conjugate samples from single rows of the detector array and interrow samples; estimate projections in a plane of reconstruction (POR) based upon a selection of the projection data from the group consisting of the conjugate samples from at least one of the single rows, the interrow samples, and combinations thereof, the selection dependent upon the selected helical pitch; weight samples of the projection data according to a distance between a corresponding conjugate sampling pair and corresponding interrow sampling pair when a combination of the conjugate samples from at least one of the single rows and the inter-row samples is selected; and filter and backproject the weighted samples to reconstruct at least one image of the object.

In yet another embodiment of the present invention, there is provided a machine-readable medium having recorded thereon instructions configured to direct a computer to input projection data acquired from a helical scan of the object at a selected pitch utilizing a computed tomographic imaging system having a multislice detector array with a plurality of rows, the projection data including both conjugate samples from single rows of the detector array and interrow samples; reconstruct an image of the object utilizing the conjugate samples; reconstruct an image of the object utilizing the interrow samples; and combine the image reconstructed utilizing the conjugates samples and the image reconstructed utilizing the interrow samples according to a pitch-dependent weighting function.

The above-described embodiments of the present invention provide improved slice sensitivity profiles (SSPs) for reconstructions at low helical pitches and a decreased effect of partial volume. In addition, contrast for small structures is maintained.

DETAILED DESCRIPTION OF THE INVENTION

Figure 1:
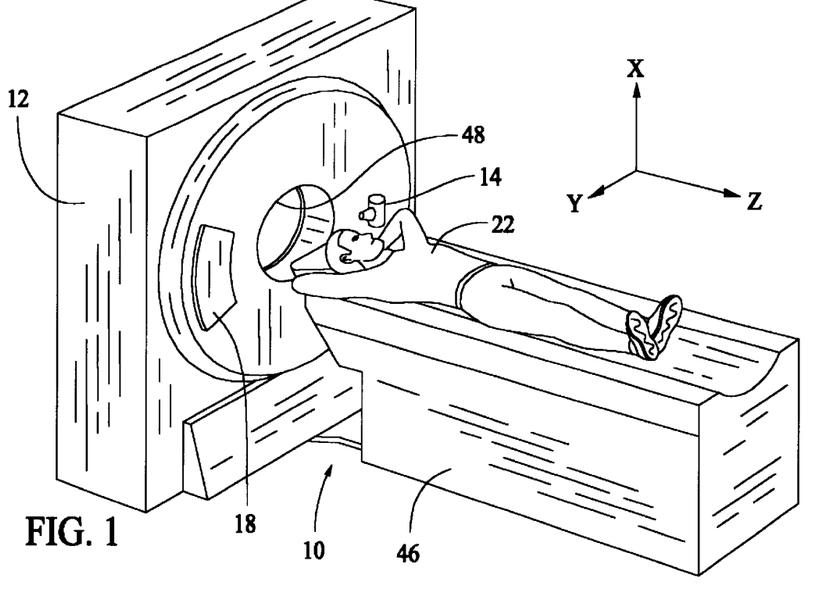
FIG. 1 is a pictorial view of a CT imaging system.
Figure 2:
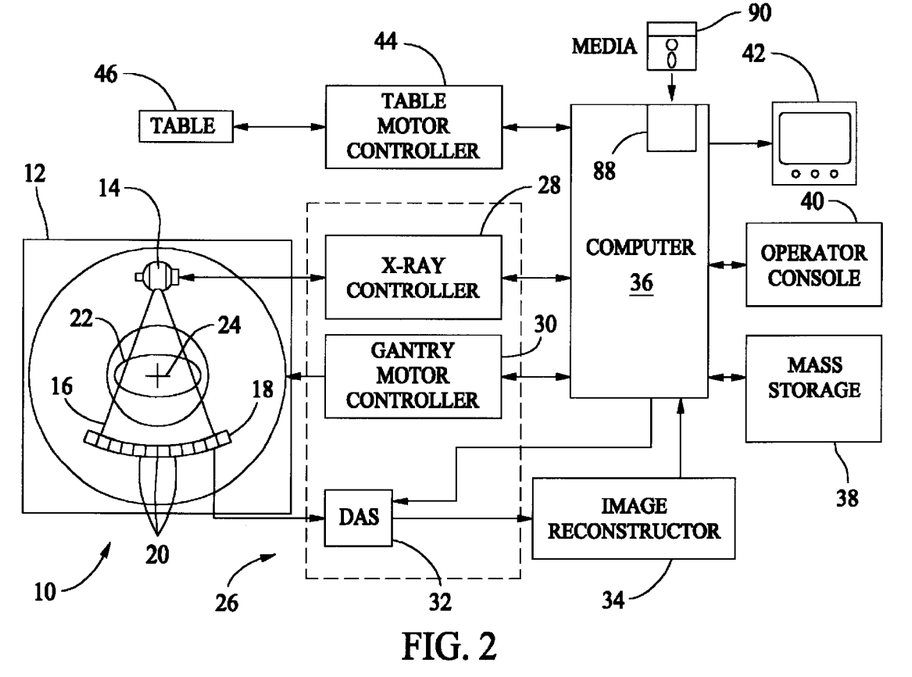
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. In one embodiment, detector array 18 is fabricated in a multi-slice configuration. In a multi-slice configuration, detector array 18 has a plurality of rows of detector elements or cells 20, only one of which is shown in FIG. 2. One or more additional rows of detector elements 20 in such configurations are arranged parallel to the illustrated row, and each row is transverse to the translation direction of patient 22 (i.e., the z-axis or patient axis).

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements or cells 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. In a helical scan as performed in some embodiments of the present invention, table 46 moves while projection data is being collected and gantry 12 is rotating. The "helical pitch" is a measure of the amount of movement of table 46 per rotation of gantry 12.

Figure 3:
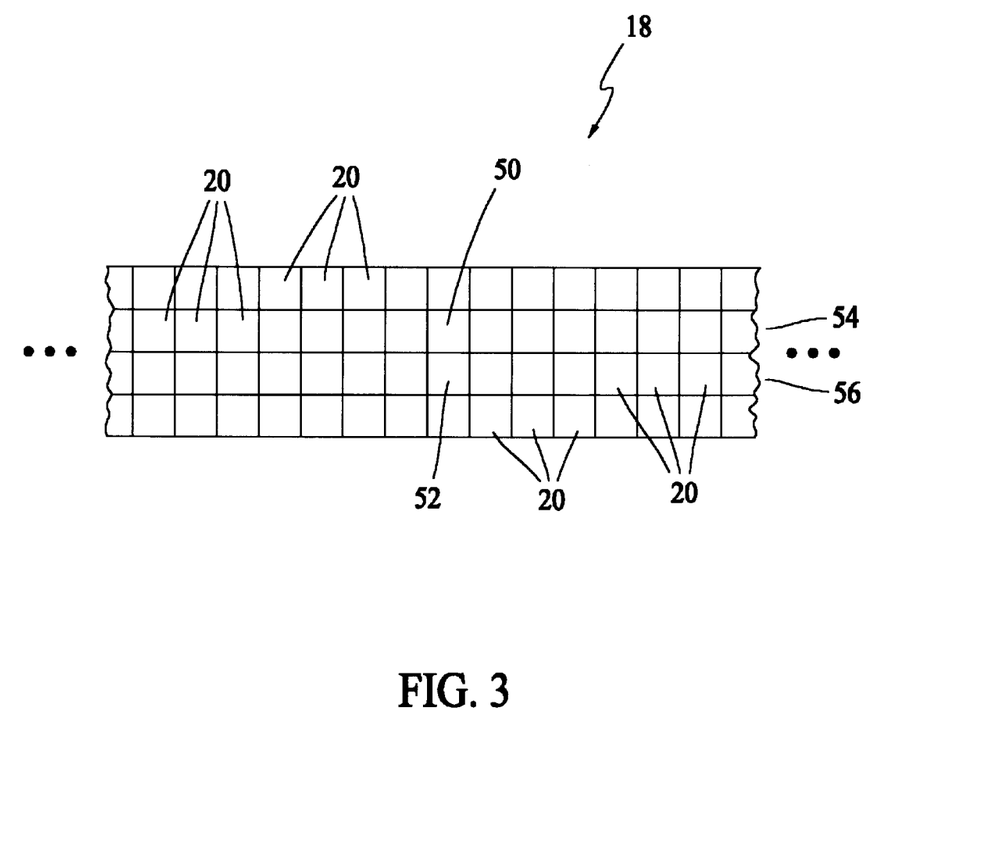
FIG. 3 is a top view of a portion of a multislice detector array.
Figure 4:
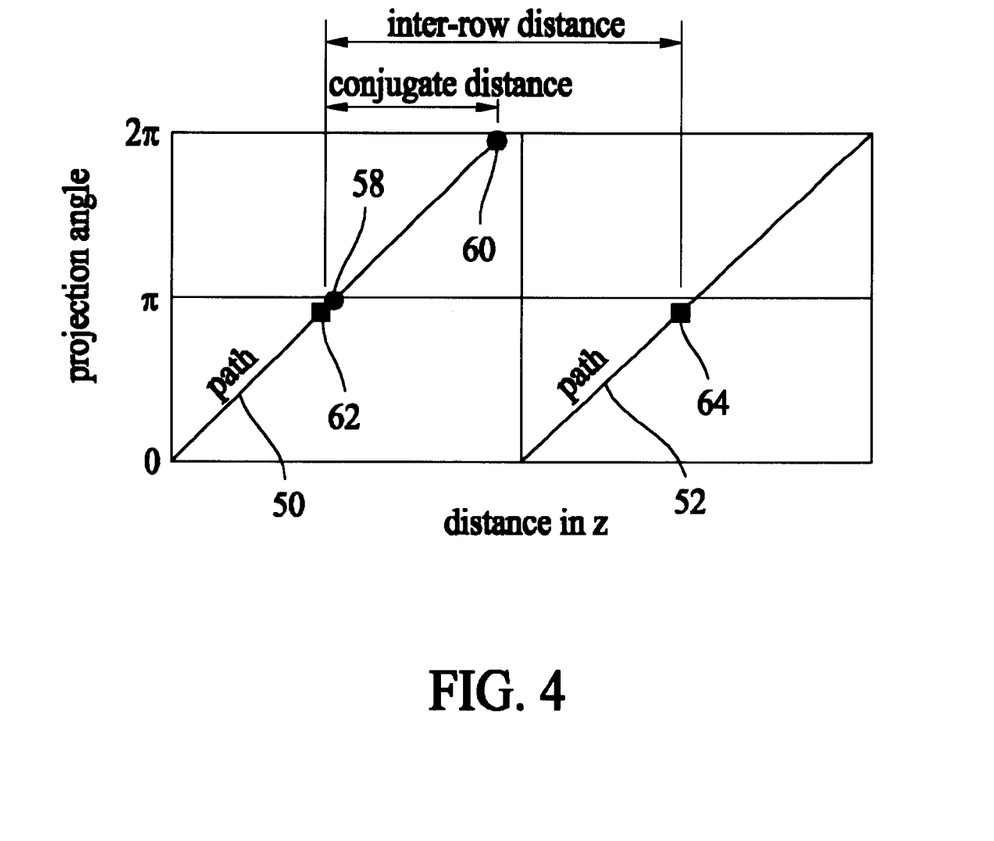
FIG. 4 is a plot of a sampling pattern for two iso-channels of neighboring detector rows shown in the partial view of the detector array of FIG. 3.

At lower helical pitch a distance between two elements or cells 20 from neighboring rows of detector array 18 is much larger than a distance between two conjugate samples from the same detector 18 row. For illustration, FIG. 3 is a representation of a portion of a multislice detector array 18. Two iso-channels 50 and 52 are indicated from neighboring detector rows 54 and 56, respectively. (An "iso-channel" is a detector element 20 that intersects a line that passes through the focal point of the x-ray beam and an iso-center of imaging system 10. A y-direction is defined by a ray from the focal point perpendicular to this z-axis, and a third axis perpendicular to both the y- and z-directions is defined as a x-direction. Detector rows 54 and 56, in one embodiment, form slightly curved arcs, but are considered to be generally oriented in the x-direction.) FIG. 4 is a plot of a sampling pattern for two iso-channels 50, 52 of neighboring detector 18 rows 54, 56, respectively, which are shown in the partial view of detector 18 in FIG. 3. A helical pitch of less than 1:1 is illustrated in FIG. 4, in which a distance a detector channel (i.e., detector element) travels in a $2\pi$ rotation is less than a distance to neighboring rows. Dots 58 and 60 represent a conjugate sample pair of the first detector 18 row 54. Squares 62 and 64 represent an inter-row interpolation pair, in this case, between rows 54 and 56. A distance between conjugate samples 58 and 60 (i.e., a "conjugate distance") is shorter than a distance between inter-row samples 62 and 64 (i.e., "inter-row distance"). Use of conjugate samples 58 and 60 should provide better interpolation results. Therefore, in one embodiment of the present invention, conjugate samples 58 and 60 are used for image reconstruction at this pitch rather than inter-row samples 62 and 64.

For helical scans, table 46 travels a distance in z that is proportional to projection angle $\beta$. Thus, in one embodiment, an estimation of the sample pair distance in z is carried out by calculating projection angle differences. An angular difference of any conjugate samples is written $\pi-2\gamma$, where $\gamma$ represents the detector angle. Although the angular difference is channel-dependent, an average distance is $\pi$. Thus, on the average, the distance in z between conjugate samples such as 58 and 60 is one-half of the product of the helical pitch and the detector aperture. This distance increases linearly with respect to the helical pitch. On the other hand, a distance between two inter-row samples such as 62 and 64 is constant and equals the detector aperture. The two samples approach a balance at a helical pitch of approximately 2:1.

Figure 5:
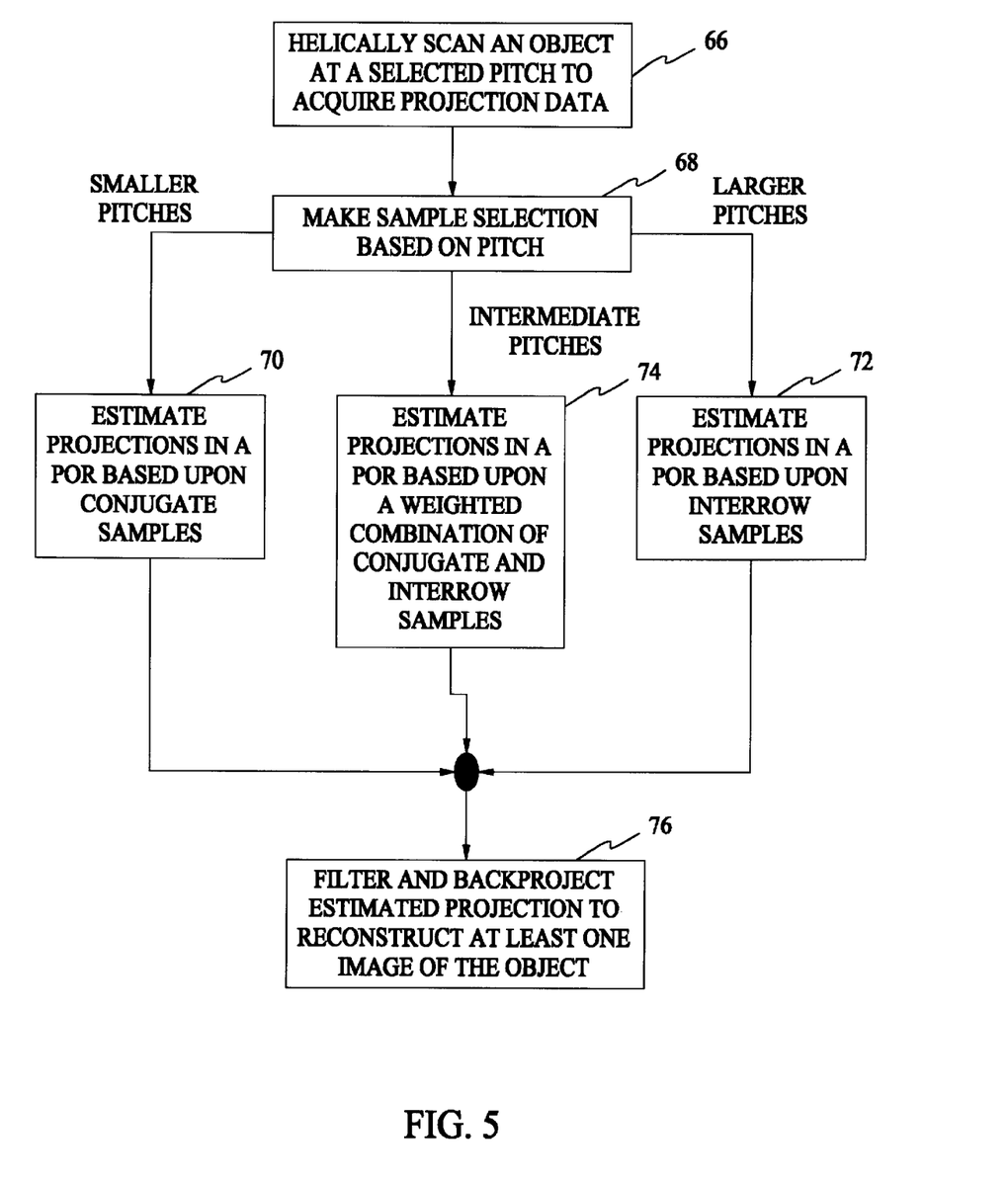
FIG. 5 is a flow chart representative of one embodiment of the present invention in which samples used to estimate projections is dependent upon a helical pitch used to scan an object.

In one embodiment and referring to FIG. 5, an object 22 is helically scanned 66 at a selected helical pitch to acquire projection data. The pitch is selected from a range having smaller values, intermediate values (i.e., those around equilibrium), and larger values. A sample selection 68 is made depending upon the size of the selected pitch. Estimates 70 of projections at a plane of reconstruction (POR) for smaller helical pitches utilize only conjugate samples such as 58 and 60 from the same detector 18 row. At large helical pitches, only inter-row samples such as 62 and 64 from neighboring rows are used to estimate projections 72. For the intermediate pitch range around equilibrium, both conjugate samples such as 58 and 60 and inter-row samples such as 62 and 64 are used to estimate projections 74. In one embodiment, a weighted combination of conjugate and interrow samples are used for the intermediate pitch range. Filtering and backprojection 76 of the estimated projections is used to reconstruct at least one image of the object.

In one embodiment, additional weights are placed on two sets of helical weights. For conjugate samples, a known helical weight is selected, such as from those used for single slice CT image reconstruction, which itself relies solely on conjugate samples from a single row. For example, helical weights are used from known helical extrapolative (HE) or helical interpolative (HI) image reconstruction methods. Weights for conjugate samples for detector row k are written as $\xi_{conj}(\gamma, \beta, k)$, and inter-row interpolation weights are written as $\xi_{inter}(\gamma, \beta, k)$. The latter weighting function includes not only the linear interpolation used to estimate projections at POR, but also half-scan (or other weights) applied to suppress projection inconsistencies. The final combined weight, written as $w(\gamma, \beta, k)$, is the weighted sum of the two weights, in which weighting function $\eta(p)$ is a helical pitch p dependent function. The final combined weight w(γ, β, k) is written:

$$w(\gamma, \beta, k) = [1-\eta(p)]\xi_{conj}(\gamma, \beta, k) + \eta(p)\xi_{inter}(\gamma, \beta, k),$$

where:

$$\eta(p) = \begin{cases} 0, & 0 \le p < p_1 \\ f(p), & p_1 \le p < p_2 \\ 1 & p \ge p_2, \end{cases}$$

$p_1$ and $p_2$ are parameters; and $f(p)$ is a monotonically increasing function of p.

In one embodiment, $p_1 = 1.5$ and $p_2 = 2.5$. Also, in one embodiment:

$$f(p) = \frac{p - p_1}{p_2 - p_1}.$$

Figure 6:
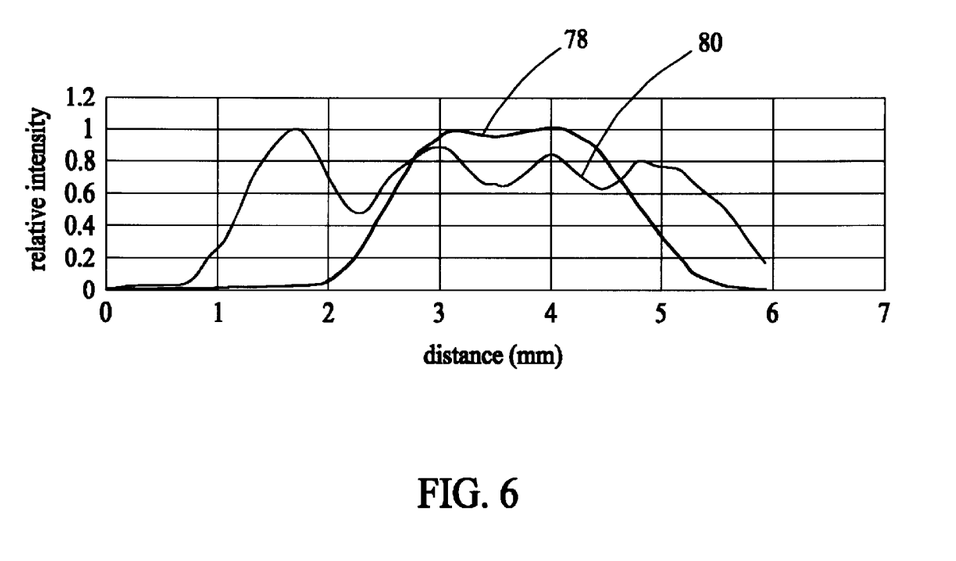
FIG. 6 is a graph on which are plotted slice sensitivity profiles for a 2.5 mm slice thickness at 0.5:1 helical pitch, one representing a embodiment of the present invention and the other representing a multislice half-scan algorithm.

In one embodiment, weighting function w(γ, β, k) is applied to the projection samples prior to filtering and backprojecting. Line 78 in FIG. 6 is a graph of a slice sensitivity profile for a 2.5 mm slice thickness at 0.5:1 helical pitch utilizing this embodiment. Line 80, for comparison, is a profile for a multi-slice half-scan algorithm for the same slice thickness and helical pitch. Data for FIG. 6 was obtained by first scanning a thin-plate phantom, and images were subsequently reconstructed at 0.1 mm increments. Intensities of the thin plate were then plotted as a function of z-location. It is clear that the profile represented by line 78 represents a significant improvement over the profile represented by line 80. More particularly, there are fewer peaks and valleys in the profile represented by line 78 and the full-width-at-half-maximum (FWHM) is much closer to the targeted slice thickness of 2.5 mm. Thus, the embodiment of the present invention represented by line 78 provides a much improved slice sensitivity profile, as compared to the multi-slice half-scan algorithm represented by line 80. In particular, better contrast for small structures and a decreased effect of partial volume are obtained.

Figure 7:
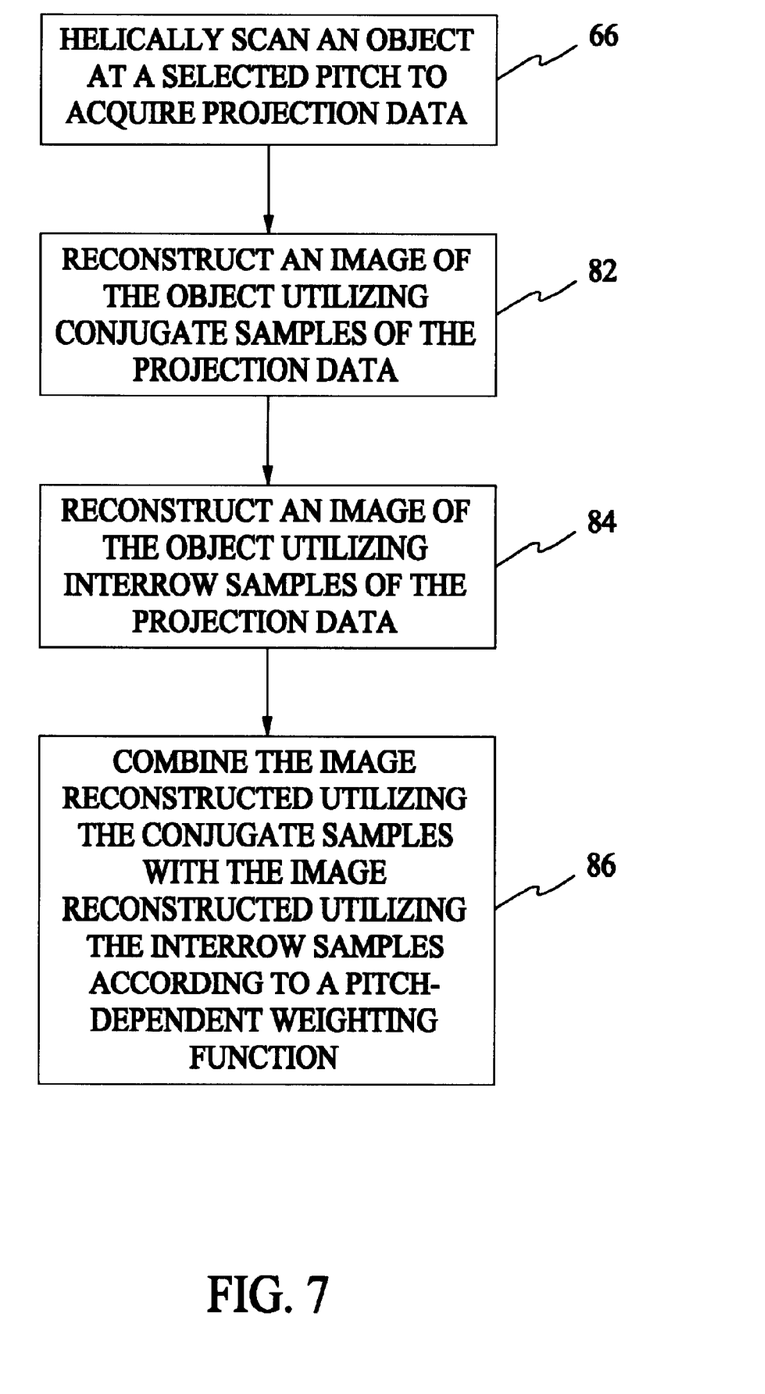
FIG. 7 is a flow chart of an embodiment of the present invention in which a plurality of images of an object are reconstructed and then combined into a single image according to a pitch-dependent weighting function.

In one embodiment and referring to FIG. 7, reconstructed images are weighted rather than projection samples, taking advantage of the linearity of the filtered backprojection operation. In this embodiment, after an object 22 is scanned 68, an image is reconstructed 82 utilizing conjugate samples of the acquired projection data and an image is also reconstructed 84 utilizing interrow samples of the acquired projection data. The images thus reconstructed are then combined 86 into a single image using a pitch-dependent weighting function. In one embodiment, the steps shown in FIG. 7 are performed only for intermediate pitches around an equilibrium pitch. Otherwise, only conjugate samples are used for smaller pitches and only interrow samples are used for larger pitches.

In another embodiment, the weighting function is determined on a sample-by-sample basis, based on a distance between a conjugate sampling pair and an inter-row sampling pair. The sampling pair that has the smaller distance is treated preferentially, such as by utilizing the additional weighting function w(γ, β, k) described above.

In one embodiment of the present invention, imaging system 10 itself is configured to perform one or more embodiments of the invention as represented by the methods herein described. This configuration utilizes combination of hardware, software and/or firmware. For example, a method embodiment is performed utilizing a suitably configured DAS 32, image reconstructor 34, computer 36, and/or mass storage device 38, optionally in conjunction with console 40. Images thus produced are displayed on display device 42. In another embodiment, reconstruction of projection data is performed utilizing hardware separate from scanning imaging system 10 from data acquired earlier by imaging system 10. In one embodiment, this hardware includes a general purpose computer (for example, a personal computer or workstation) configured to perform one or more embodiments of the invention as represented by the methods herein described. In embodiments in which the computer or workstation includes a media reader, a machine-readable medium is provided that is encoded with instructions for a computer to read projection data obtained from an imaging system 10 and to reconstruct images therefrom. Data acquired by a separate imaging system 10 is read from media or from a network.

Referring to FIG. 1, in one embodiment, computer 36 of imaging system 10, also is equipped with a media reader 88 for reading instructions recorded on medium 90. Suitable computer readable media 90 include, but are not limited to, CD-ROMs, floppy diskettes, and digital magnetic tape. Thus, embodiments of the present invention also include media 90 upon which computer-readable instructions are recorded to instruct a computer such as computer 36 or a separate workstation to perform an embodiment of the inventive method described herein.

It will be evident that the above-described embodiments of the present invention provide improved slice sensitivity profiles (SSPs) for reconstructions at low helical pitches and a decreased effect of partial volume. In addition, contrast for small structures is maintained.

As used herein, an element or step recited in the singular and preceded with the word "a" or "an" should be understood as not excluding plural said elements or steps, unless such exclusion is explicitly recited. Furthermore, passages referring to "one embodiment" of the present invention are not intended to be interpreted as excluding the existence of additional embodiments that also incorporate the recited features.

Also as used herein, the phrase "reconstructing an image" is not intended to exclude those embodiments in which data representing or an image is generated but a viewable image is not. However, many embodiments generate (or are configured to generate) at least one viewable image.

While the invention has been described in terms of various specific embodiments, those skilled in the art will recognize that the invention call be practiced with modification within the spirit and scope of the claims.

What is claimed is:

1. A method for reconstructing an image of an object utilizing a computed tomographic imaging system having a rotating gantry, a multirow detector array on the rotating gantry, and a radiation source on the rotating gantry configured to project a beam of radiation towards the detector array through an object to be imaged;

said method comprising:
    helically scanning an object at a selected helical pitch to acquire projection data of the object, the projection data including conjugate samples from single rows of the detector array and interrow samples;
    estimating projections in a plane of reconstruction (POR) based upon a selection of the projection data from the group consisting of the conjugate samples from at least one of the single rows, the interrow samples, and combinations thereof, the selection dependent upon the selected helical pitch;

and filtering and backprojecting the estimated projections to reconstruct at least one image of the object.

2. A method in accordance with claim 1 wherein said estimation of projections comprises selecting the conjugate samples from the at least one of the single rows for a range of smaller helical pitches, selecting the interrow samples for a range of larger helical pitches, and selecting a combination of the conjugate samples and the interrow samples for a range of intermediate helical pitches.

3. A method in accordance with claim 1 wherein said estimation of projections comprises applying a weighting function w($\gamma$, $\beta$, k) to samples at a detector angle $\gamma$, a projection angle $\beta$, and a detector row k, the weighting function written as:

$$w(\gamma, \beta, k) = [1 - \eta(p)] \xi_{conj}(\gamma, \beta, k) + \eta(p) \xi_{inter}(\gamma, \beta, k),$$

where:

p is the selected helical pitch;

$\xi_{conj}(\gamma, \beta, k)$ is a conjugate weighting function applied to conjugate weighting functions in detector row k;

$\xi_{inter}(\gamma, \beta, k)$ is an interrow interpolation weight for detector row k;

$$\eta(p) = \begin{cases} 0, & 0 \leq p < p_1 \\ f(p), & p_1 \leq p < p_2 \\ 1 & p \geq p_2, \end{cases}$$

$p_1$ and $p_2$ are parameters; and $f(p)$ is a monotonically increasing function of p.

4. A method in accordance with claim 3 wherein $f(p)$ is written:

$$f(p) = \frac{p - p_1}{p_2 - p_1}.$$

5. A method in accordance with claim 3 wherein $p_1 = 1.5$ and $p_2 = 2.5$.

6. A method for reconstructing an image of an object utilizing a computed tomographic imaging system having a rotating gantry, a multirow detector array on the rotating gantry, and a radiation source on the rotating gantry configured to project a beam of radiation towards the detector array through an object to be imaged;

said method comprising:
helically scanning an object at a selected helical pitch to acquire projection data of the object, the projection data including conjugate samples from single rows of the detector array and interrow samples;
estimating projections in a plane of reconstruction (POR) based upon a selection of the projection data from the group consisting of the conjugate samples from at least one of the single rows, the interrow samples, and combinations thereof, the selection dependent upon the selected helical pitch;
weighting samples of the projection data according to a distance between a corresponding conjugate sampling pair and corresponding interrow sampling pair when a combination of the conjugate samples from at least one of the single rows and the interrow samples is selected; and
filtering and backprojecting the weighted samples to reconstruct at least one image of the object.

7. A method for reconstructing an image of an object utilizing a computed tomographic imaging system having a rotating gantry, a multirow detector array on the rotating gantry, and a radiation source on the rotating gantry configured to project a beam of radiation towards the detector array through an object to be imaged;

said method comprising:
helically scanning an object at a selected helical pitch to acquire projection data of the object, the projection data including conjugate samples from single rows of the detector array and interrow samples;
reconstructing an image of the object utilizing the conjugate samples;
reconstructing an image of the object utilizing the interrow samples; and
combining the image reconstructed utilizing the conjugates samples and the image reconstructed utilizing the interrow samples according to a pitch-dependent weighting function.

8. A computed tomographic (CT) imaging system having a rotating gantry, a multirow detector array on said rotating gantry, and a radiation source on said rotating gantry configured to project a beam of radiation towards said detector array through an object to be imaged;

said system configured to:
helically scan an object at a selected helical pitch to acquire projection data of the object, said projection data including conjugate samples from single rows of said detector array and interrow samples;
estimate projections in a plane of reconstruction (POR) based upon a selection of said projection data from the group consisting of said conjugate samples from at least one of said single rows, said interrow samples, and their combination, said selection dependent upon the selected helical pitch;
and filter and backproject said estimated projections to reconstruct at least one image of the object.

9. A system in accordance with claim 8 wherein to estimate projections, said system is configured to select said conjugate samples from said at least one of said single rows for a range of smaller helical pitches, select said interrow samples for a range of larger helical pitches, and select a combination of said conjugate samples and said interrow samples for a range of intermediate helical pitches.

10. A system in accordance with claim 8 wherein to estimate projections, said system is configured to apply a weighting function w($\gamma$, $\beta$, k) to samples at detector angle $\gamma$, projection angle $\beta$, and detector row k, said weighting function written as:

$$w(\gamma, \beta, k) = [1 - \eta(p)] \xi_{conj}(\gamma, \beta, k) + \eta(p) \xi_{inter}(\gamma, \beta, k),$$

where:

p is the selected helical pitch;

$\xi_{conj}(\gamma, \beta, k)$ is a conjugate weighting function applied to conjugate weighting functions in detector row k;

$\xi_{inter}(\gamma, \beta, k)$ is an interrow interpolation weight for detector row k;

$$\eta(p) = \begin{cases} 0, & 0 \leq p < p_1 \\ f(p), & p_1 \leq p < p_2 \\ 1 & p \geq p_2, \end{cases}$$

$p_1$ and $p_2$ are parameters; and $f(p)$ is a monotonically increasing function of p.

11. A system in accordance with claim 10 wherein $f(p)$ is written:

$$f(p) = \frac{p - p_1}{p_2 - p_1}.$$

12. A system in accordance with claim 11 wherein $p_1$=1.5 and $p_2$=2.5.

13. A computed tomographic (CT) imaging system having a rotating gantry, a multirow detector array on said rotating gantry, and a radiation source on said rotating gantry configured to project a beam of radiation towards said detector array through an object to be imaged;
said system configured to:
helically scan an object at a selected helical pitch to acquire projection data of the object, said projection data including conjugate samples from single rows of said detector array and interrow samples;
estimate projections in a plane of reconstruction (POR) based upon a selection of said projection data from the group consisting of said conjugate samples from at least one of said single rows, said interrow samples, and combinations thereof, said selection dependent upon the selected helical pitch;
weight samples of said projection data according to a distance between a corresponding conjugate sampling pair and corresponding interrow sampling pair when a combination of said conjugate samples from at least one of said single rows and said inter-row samples is selected;
and filter and backproject said weighted samples to reconstruct at least one image of the object.

14. A computed tomographic (CT) imaging system having a rotating gantry, a multirow detector array on said rotating gantry, and a radiation source on said rotating gantry configured to project a beam of radiation towards said detector array through an object to be imaged;
said system configured to:
helically scan an object at a selected helical pitch to acquire projection data of the object, said projection data including conjugate samples from single rows of said detector array and interrow samples;
reconstruct an image of the object utilizing said conjugate samples;
reconstruct an image of the object utilizing said interrow samples; and
combine said image reconstructed utilizing said conjugates samples and said image reconstructed utilizing said interrow samples according to a pitch-dependent weighting function.

15. A device for reconstructing an image of an object utilizing projection data acquired from a helical scan of the object at a selected pitch utilizing a computed tomographic imaging system having a multislice detector array with a plurality of rows, the projection data including both conjugate samples from single rows of the detector array and interrow samples;
said device configured to:
estimate projections in a plane of reconstruction (POR) based upon a selection of the projection data from the group consisting of the conjugate samples from at least one of the single rows, the interrow samples, and combinations thereof, the selection dependent upon the selected helical pitch; and
filter and backproject said estimated projections to reconstruct at least one image of the object.

16. A device in accordance with claim 15 wherein to estimation projections, said device is configured to select the conjugate samples from the at least one of the single rows for a range of smaller helical pitches, select the interrow samples for a range of larger helical pitches, and select a combination of the conjugate samples and the interrow samples for a range of intermediate helical pitches.

17. A device in accordance with claim 15 wherein to estimate projections, said device is configured to apply a weighting function $w(\gamma, \beta, k)$ to samples at a detector angle $\gamma$, a projection angle $\beta$, and a detector row k, the weighting function written as:

$$w(\gamma, \beta, k) = [1 - \eta(p)]\xi_{conj}(\gamma, \beta, k) + \eta(p)\xi_{inter}(\gamma, \beta, k),$$

where:
p is the selected helical pitch;
$\xi_{conj}(\gamma, \beta, k)$ is a conjugate weighting function applied to conjugate weighting functions in detector row k;
$\xi_{inter}(\gamma, \beta, k)$ is an interrow interpolation weight for detector row k;

$$\eta(p) = \begin{cases} 0, & 0 \le p < p_1 \\ f(p), & p_1 \le p < p_2 \\ 1 & p \ge p_2, \end{cases}$$

$p_1$ and $p_2$ are parameters; and
$f(p)$ is a monotonically increasing function of p.

18. A device in accordance with claim 17 wherein $f(p)$ is written:

$$f(p) = \frac{p - p_1}{p_2 - p_1}.$$

19. A device in accordance with claim 17 wherein $p_1$=1.5 and $p_2$=2.5.

20. A device for reconstructing an image of an object utilizing projection data acquired from a helical scan of the object at a selected pitch utilizing a computed tomographic imaging system having a multislice detector array with a plurality of rows, the projection data including both conjugate samples from single rows of the detector array and interrow samples;
said device configured to:
estimate projections in a plane of reconstruction (POR) based upon a selection of the projection data from the group consisting of the conjugate samples from at least one of the single rows, the interrow samples, and combinations thereof, the selection dependent upon the selected helical pitch;
weight samples of the projection data according to a distance between a corresponding conjugate sampling pair and corresponding interrow sampling pair when a combination of the conjugate samples from at least one of the single rows and the interrow samples is selected; and
filter and backproject said weighted samples to reconstruct at least one image of the object.

21. A device for reconstructing an image of an object utilizing projection data acquired from a helical scan of the object at a selected pitch utilizing a computed tomographic imaging system having a multislice detector array with a plurality of rows, the projection data including both conjugate samples from single rows of the detector array and interrow samples;

said device configured to:
estimate projections in a plane of reconstruction (POR) based upon a selection of the projection data from the group consisting of the conjugate samples from at least one of the single rows, the interrow samples, and combinations thereof, the selection dependent upon the selected helical pitch;
reconstruct an image of the object utilizing the conjugate samples;
reconstruct an image of the object utilizing the interrow samples; and
combine said image reconstructed utilizing the conjugates samples and said image reconstructed utilizing the interrow samples according to a pitch-dependent weighting function.

22. A machine-readable medium having recorded thereon instructions configured to direct a computer to:
input projection data acquired from a helical scan of the object at a selected pitch utilizing a computed tomographic imaging system having a multislice detector array with a plurality of rows, the projection data including both conjugate samples from single rows of the detector array and interrow samples;
estimate projections in a plane of reconstruction (POR) based upon a selection of the projection data from the group consisting of the conjugate samples from at least one of the single rows, the interrow samples, and combinations thereof, the selection dependent upon the selected helical pitch; and
filter and backproject said estimated projections to reconstruct at least one image of the object.

23. A machine-readable medium in accordance with claim 22 wherein to estimate projections, said machine-readable medium has instructions recorded thereon configured to instruct the computer to select conjugate samples from said at least one of said single rows for a range of smaller helical pitches, select interrow samples for a range of larger helical pitches, and select a combination of said conjugate samples and said interrow samples for a range of intermediate helical pitches.

24. A machine-readable medium in accordance with claim 22 wherein to estimate projections, said machine-readable medium has instructions recorded thereon configured to instruct the computer to apply a weighting function w(γ, β, k) to samples at detector angle γ, projection angle β, and detector row k, said weighting function written as:

$$w(\gamma, \beta, k) = [1-\eta(p)]\xi_{conj}(\gamma, \beta, k) + \eta(p)\xi_{inter}(\gamma, \beta, k),$$

where:
p is the selected helical pitch;
$\xi_{conj}(\gamma, \beta, k)$ is a conjugate weighting function applied to conjugate weighting functions in detector row k;
$\xi_{inter}(\gamma, \beta, k)$ is an interrow interpolation weight for detector row k;

$$\eta(p) = \begin{cases} 0, & 0 \le p < p_1 \\ f(p), & p_1 \le p < p_2 \\ 1 & p \ge p_2, \end{cases}$$

$p_1$ and $p_2$ are parameters; and
$f(p)$ is a monotonically increasing function of p.

25. A system in accordance with claim 24 wherein $f(p)$ is written:

$$f(p) = \frac{p - p_1}{p_2 - p_1}.$$

26. A machine-readable medium in accordance with claim 24 wherein $p_1$=1.5 and $p_2$=2.5.

27. A machine-readable medium having recorded thereon instructions configured to direct a computer to:
input projection data acquired from a helical scan of the object at a selected pitch utilizing a computed tomographic imaging system having a multislice detector array with a plurality of rows, the projection data including both conjugate samples from single rows of the detector array and interrow samples;
estimate projections in a plane of reconstruction (POR) based upon a selection of the projection data from the group consisting of the conjugate samples from at least one of the single rows, the interrow samples, and combinations thereof, the selection dependent upon the selected helical pitch;
weight samples of said projection data according to a distance between a corresponding conjugate sampling pair and corresponding interrow sampling pair when a combination of said conjugate samples from at least one of said single rows and said inter-row samples is selected; and
filter and backproject said weighted samples to reconstruct at least one image of the object.

28. A machine-readable medium having recorded thereon instructions configured to direct a computer to:
input projection data acquired from a helical scan of the object at a selected pitch utilizing a computed tomographic imaging system having a multislice detector array with a plurality of rows, the projection data including both conjugate samples from single rows of the detector array and interrow samples;
reconstruct an image of the object utilizing said conjugate samples;
reconstruct an image of the object utilizing said interrow samples; and
combine said image reconstructed utilizing said conjugates samples and said image reconstructed utilizing said interrow samples according to a pitch-dependent weighting function.

* * * * *